United States Patent
Ikeda

(10) Patent No.: US 9,903,818 B2
(45) Date of Patent: Feb. 27, 2018

(54) SYSTEM FOR PROVISION OF ANALYSIS RESULTS, ANALYSIS TERMINAL, AND METHOD FOR PROVISION OF ANALYSIS RESULTS

(71) Applicant: IMAGINEERING, INC., Kobe-shi, Hyogo (JP)

(72) Inventor: Yuji Ikeda, Kobe (JP)

(73) Assignee: IMAGINEERING, INC., Hyogo (JP)

( * ) Notice: Subject to any disclaimer, the term of this patent is extended or adjusted under 35 U.S.C. 154(b) by 362 days.

(21) Appl. No.: 14/369,125

(22) PCT Filed: Dec. 26, 2012

(86) PCT No.: PCT/JP2012/083618
§ 371 (c)(1),
(2) Date: Aug. 26, 2014

(87) PCT Pub. No.: WO2013/099928
PCT Pub. Date: Jul. 4, 2013

(65) Prior Publication Data
US 2014/0362375 A1     Dec. 11, 2014

(30) Foreign Application Priority Data

Dec. 28, 2011 (JP) ................... 2011-289620

(51) Int. Cl.
*G01J 3/30* (2006.01)
*G01N 21/62* (2006.01)
(Continued)

(52) U.S. Cl.
CPC ............ *G01N 21/62* (2013.01); *G01N 21/63* (2013.01); *G01N 21/68* (2013.01); *G01N 21/718* (2013.01); *G01N 2201/0221* (2013.01)

(58) Field of Classification Search
CPC ........ G01N 21/62; G01N 21/73; G01N 21/68; G01J 3/443; H01J 49/105; H05H 1/30
(Continued)

(56) References Cited

U.S. PATENT DOCUMENTS

| 5,408,307 A | 4/1995 | Yamamoto et al. |
| 2003/0095266 A1* | 5/2003 | Detalle ................ G01N 21/718 356/502 |

(Continued)

FOREIGN PATENT DOCUMENTS

| JP | 64-78164 A | 3/1989 |
| JP | 2-51044 A | 2/1990 |

(Continued)

OTHER PUBLICATIONS

International Search Report dated May 14, 2013 issued in corresponding application No. PCT/JP2012/083618.

*Primary Examiner* — Abdullahi Nur
(74) *Attorney, Agent, or Firm* — Westerman, Hattori, Daniels & Adrian, LLP

(57) ABSTRACT

To implement an analysis result provision system that can acquire an analysis result of a target substance without transferring the substance when the substance is analyzed using plasma light information occurred from plasma area where the substance is turned to plasma state, a provision system of analysis result includes an analytical terminal that turns a target substance to plasma state and acquires plasma light information occurred from plasma area, and a host computer. The host computer includes host side communication part that acquires plasma light information via telecommunication line, and information analysis part that analyzes the target substance using plasma light information acquired by the host side communication part. The host side communication part transmits the analysis result of the target substance to the sender of the plasma light informa- (Continued)

tion. The analysis result is obtained by the analysis of the information analysis part using plasma light information.

18 Claims, 8 Drawing Sheets

(51) Int. Cl.
  *G01N 21/68* (2006.01)
  *G01N 21/63* (2006.01)
  *G01N 21/71* (2006.01)

(58) Field of Classification Search
  USPC .................................................. 356/300–316
  See application file for complete search history.

(56) References Cited

U.S. PATENT DOCUMENTS

2004/0247522 A1* 12/2004 Mills ...................... B01J 19/088
  423/648.1
2006/0263252 A1  11/2006 Sanchez-Olea et al.
2013/0115717 A1*  5/2013 Guo ................. G01N 33/54346
  436/501

FOREIGN PATENT DOCUMENTS

| JP | 2002-80885 A | 3/2002 |
| JP | 2003-344277 A | 12/2003 |
| JP | 2006-528782 A | 12/2006 |
| JP | 2008-164513 A | 7/2008 |
| JP | 2009-70586 A | 4/2009 |
| JP | 2009-97976 A | 5/2009 |

* cited by examiner

[Fig.1]
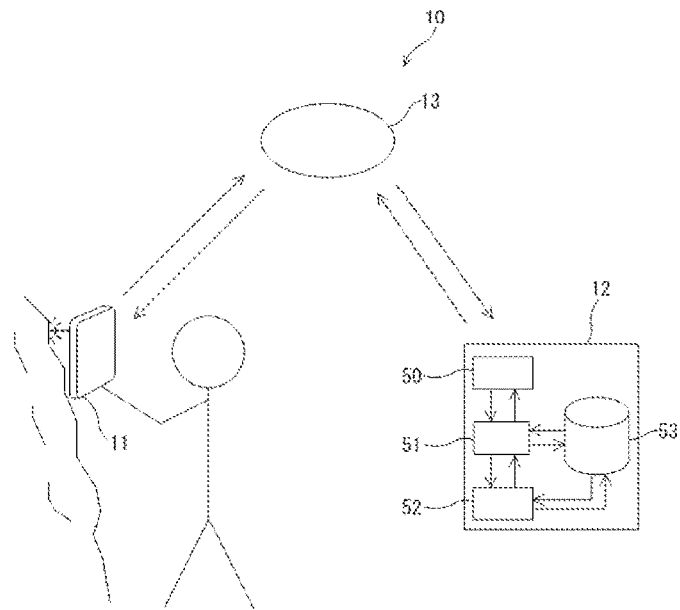
[Fig.2]
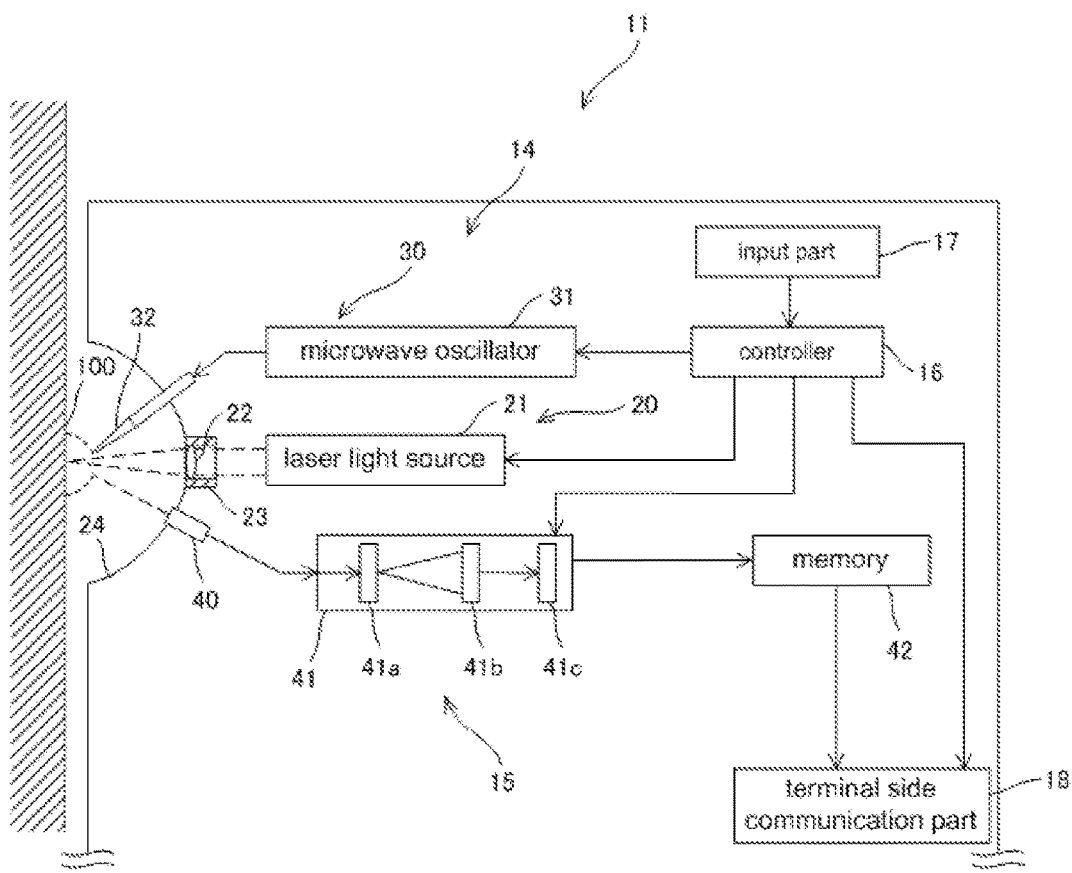

[Fig.3]
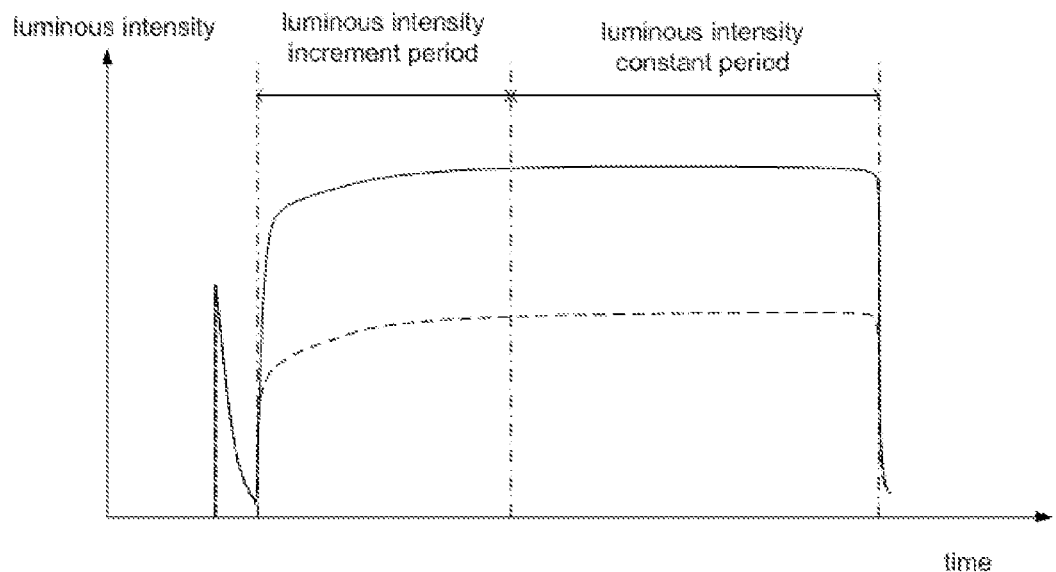
[Fig.4]
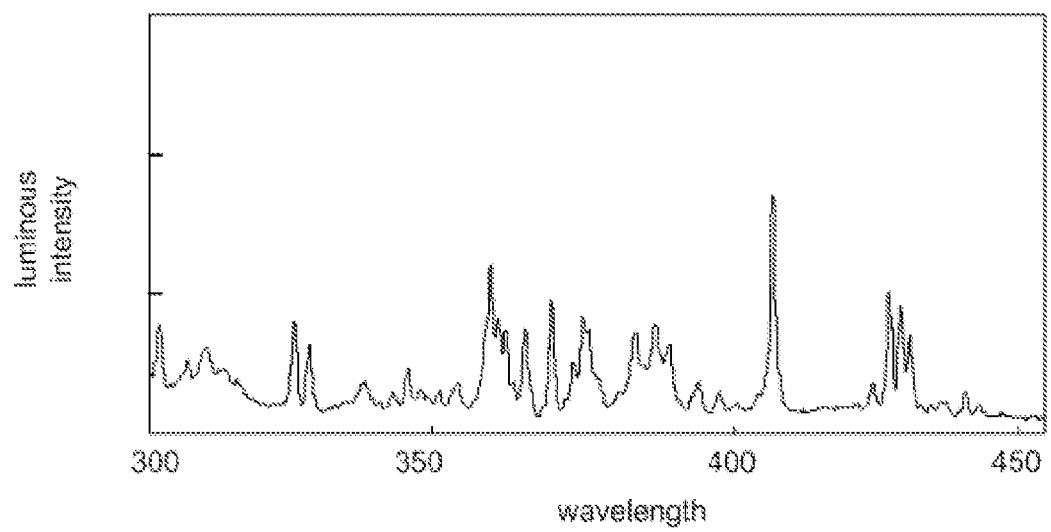

[Fig.5]
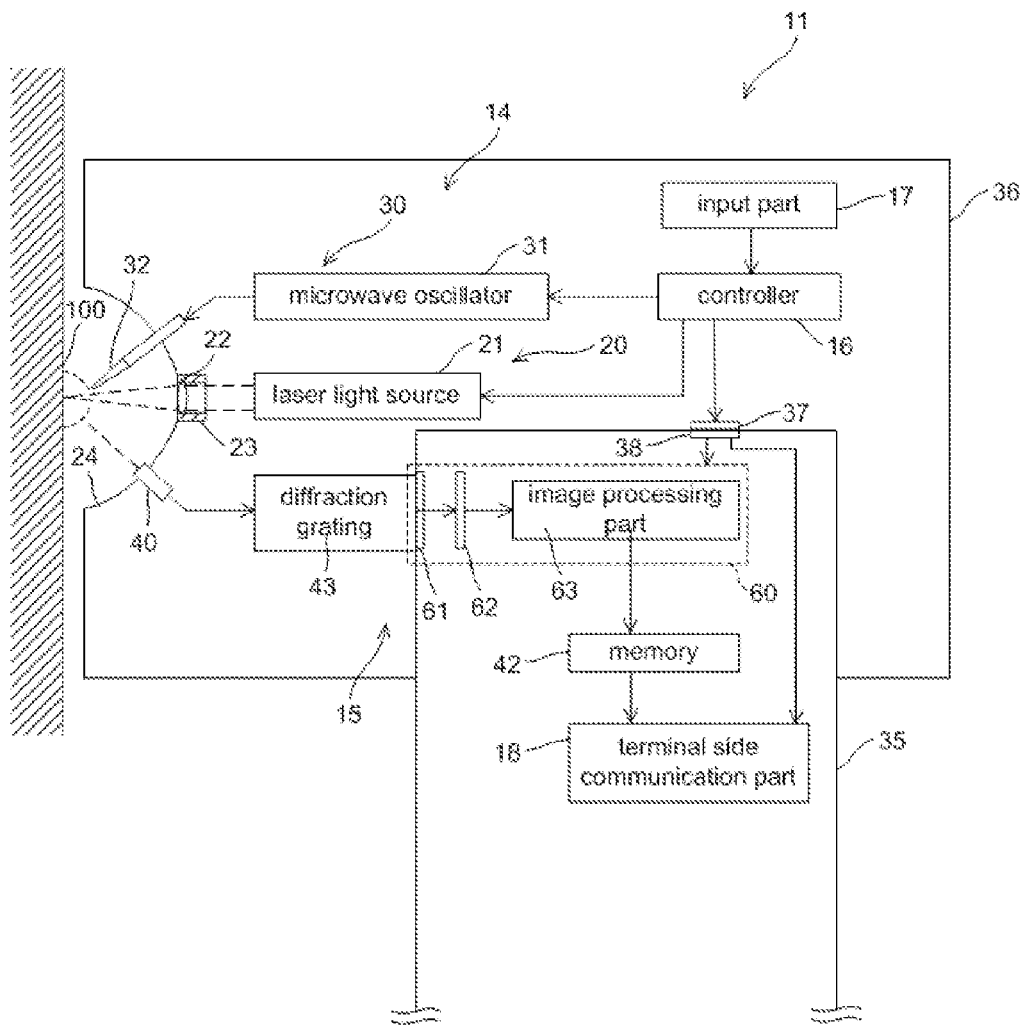

[Fig.6]
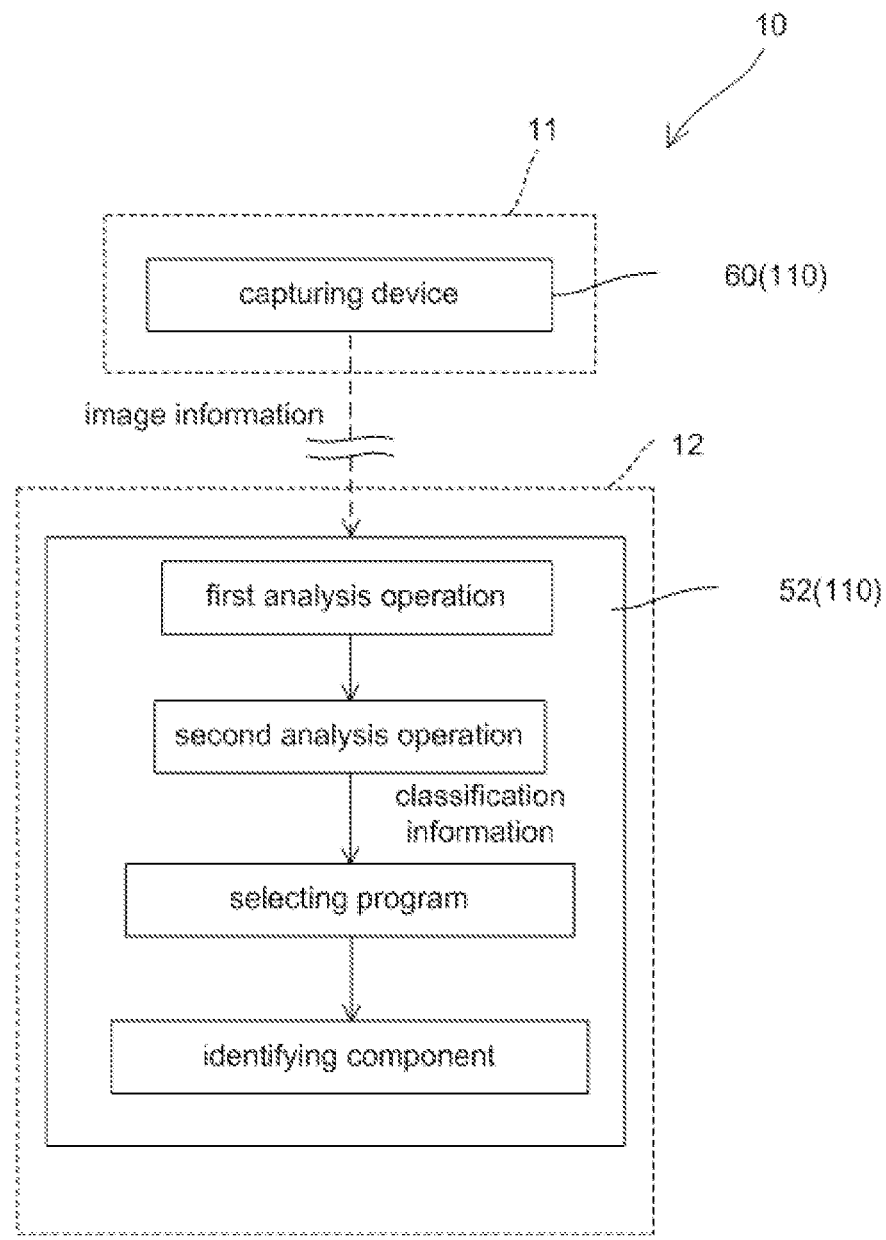

[Fig.7]
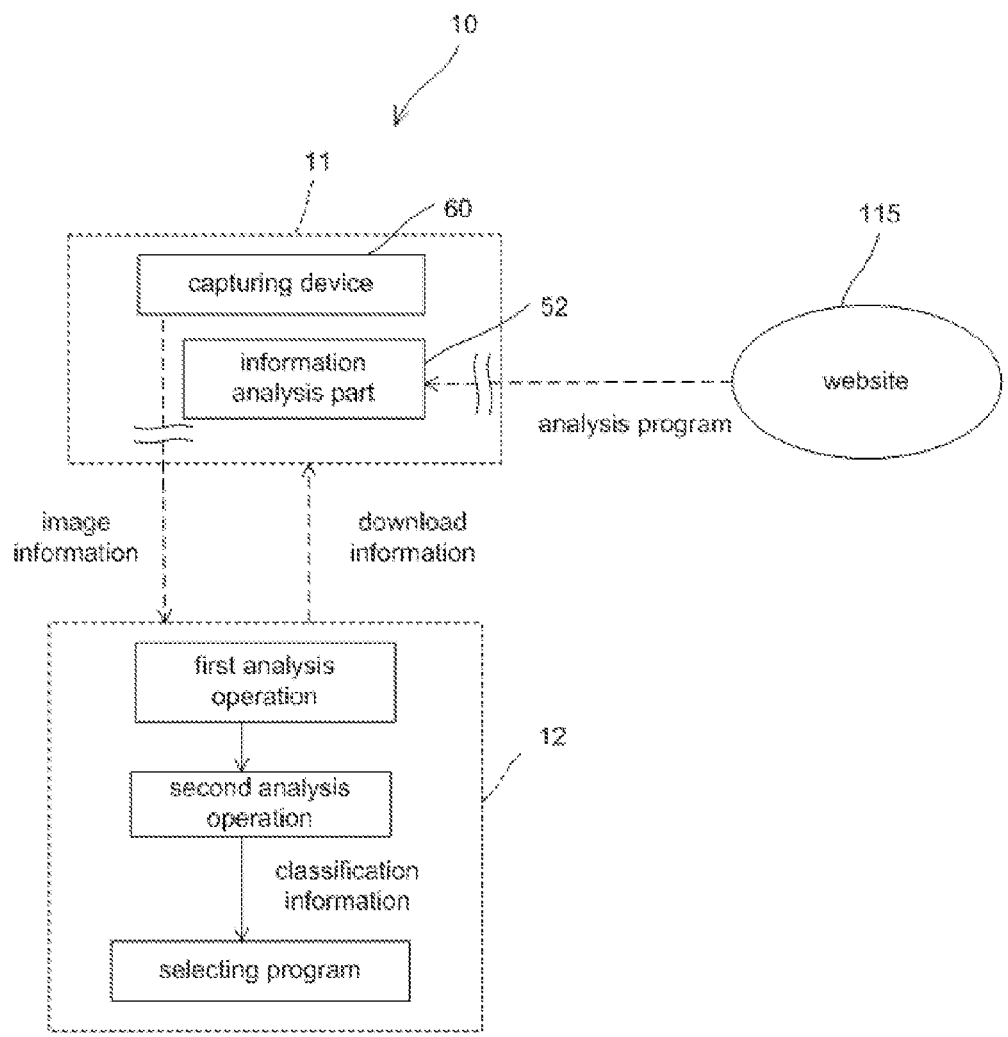

[Fig.8]
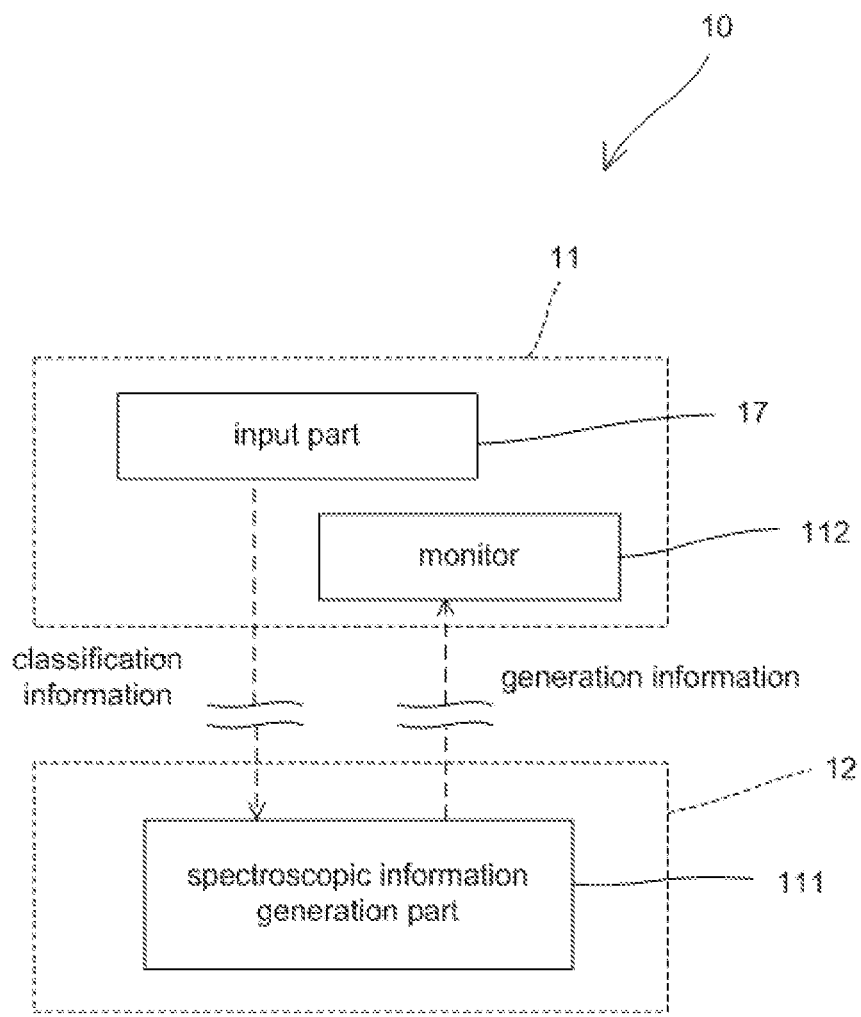

[Fig.9]
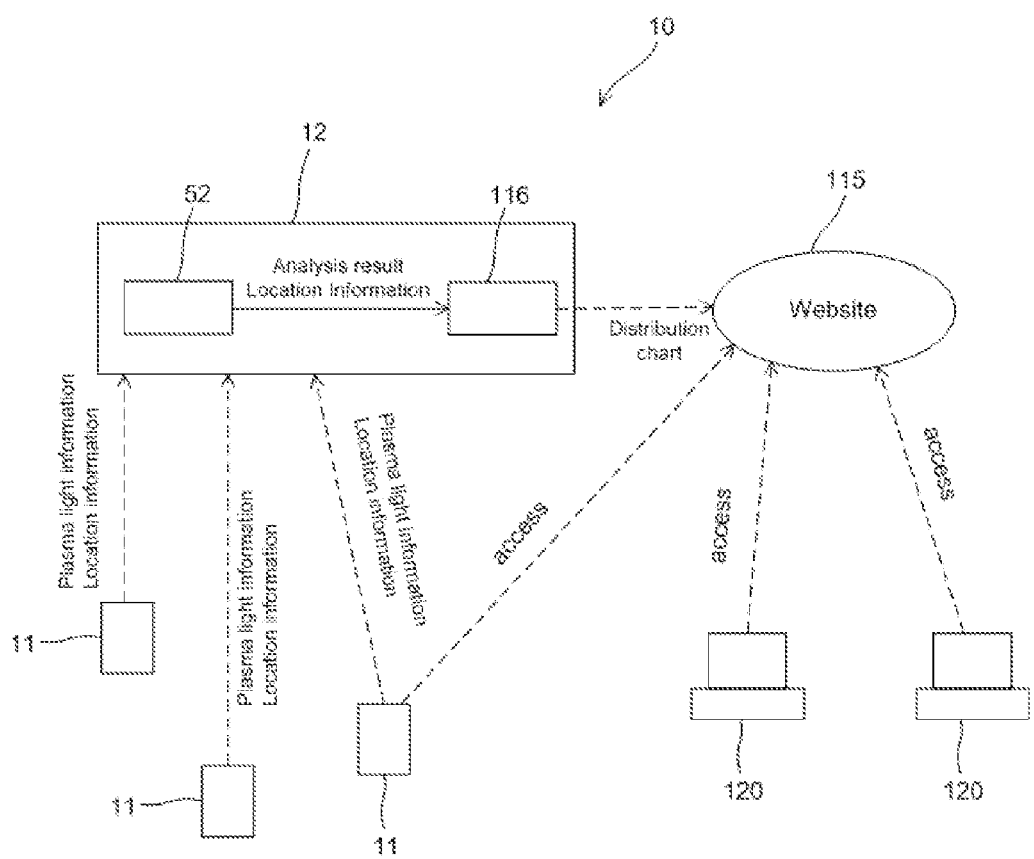

[Fig.10]
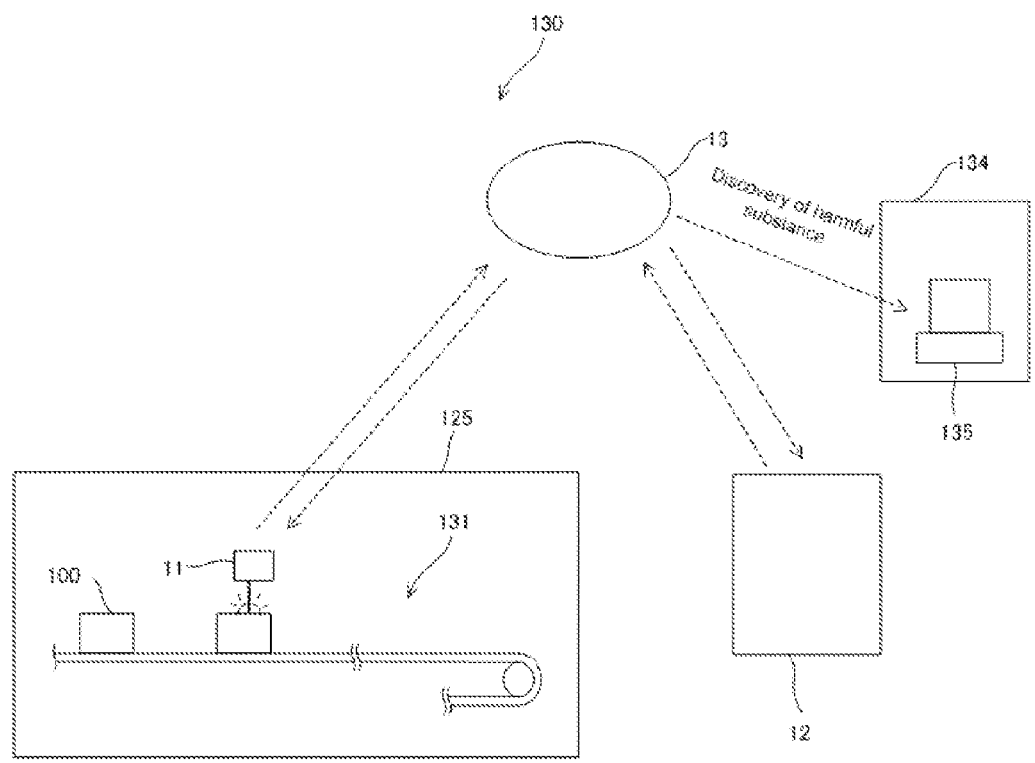

SYSTEM FOR PROVISION OF ANALYSIS RESULTS, ANALYSIS TERMINAL, AND METHOD FOR PROVISION OF ANALYSIS RESULTS

TECHNICAL FIELD

The present invention rotated to an analysis result provision system that provides analysis result of a target substance that is acquired from analysis of plasma light, analytical terminal and provision method of analysis result.

BACKGROUND

There has been known an analysis device for analyzing a target substance that uses plasma light occurred from the target substance which is in plasma state. For example, such analysis device is described in patent document L.

Specifically, patent document 1 describes a measurement device that uses Laser-Induced Breakdown Spectroscopy. This measurement device includes a plasma generation device that generates plasma using electron occurred by laser induced breakdown and microwave energy. In this plasma generation device, microwave pulses oscillated, from microwave generator are radiated from an antenna. As a result, plasma in a plasma area, where plasma is generated by laser light, expands by absorbing microwave energy.

PRIOR ART DOCUMENT

Patent Document

Patent Document 1: JP 2009-070386A1

SUMMARY OF INVENTION

Problems to be Solved

In a conventional analysis device, a target substance is analyzed by transferring the target substance to indoor such as laboratory where an analysis device is installed, and then the target substance is analyzed in the indoor. However, it would be convenient if the analysis result of the target substance can be acquired without transferring the target substance. For example, it will be convenient if the component of a mineral can be detected without transferring the mineral, or if a component attached to a person's skin can be detected on the spot.

The present invention is in view of this respect. The present invention relates to an analysis technology that analyzes a target substance by turning the target substance to a plasma state and by using the plasma light information that is occurred from this plasma area, and the objective of the present invention is to provide an analysis result provision system that can acquire an analysis result of the target substance without transferring the target substance.

Means for Solving the Problems

The first invention relates to a provision system of analysis result comprising an analytical terminal and a host computer. The analytical terminal turns a target substance to plasma state and acquires plasma light information occurred from plasma area. The host computer includes, i) host side communication part that acquires plasma light information via telecommunication line, and ii) information analysis part that analyzes the target substance using the plasma light information acquired by the host side communication part. The host side communication part transmits the analysis result of the target substance to the sender of the plasma light information. The analysis result is obtained through the analysis of the information analysis part using the plasma light information.

In the first invention, a target substance can be turned to a plasma state at the location where the target, substance exists, and then plasma light information can that is occurred from the target substance in the plasma state can be acquired using an analytical terminal. A host side communication part of a host computer receives the plasma light information acquired by the analytical terminal via telecommunication line. In the host computer, an information analysis part analyzes the target substance using the plasma light information received by the host side communication part. Then, the host side communication part sends the analysis result of the target substance obtained by the analysis of the information analysis part to the sender of the plasma light information. To analyze the target substance, a first means for turning a target substance to plasma state, a second means for acquiring plasma light information occurred from the plasma area, and a third moans for analyzing the target substance using the plasma light information. In the first invention, the first means and the second means are installed in the analytical terminal and the third means is installed in the host computer. The analysis result of the target substance is provided to a user of the analytical terminal by communicating the plasma light information and the analysis result of the target substance between the analytical terminal and the host computer using the telecommunication line.

The second invention relates to the first invention where the analytical terminal has a terminal side communication part that sends the plasma light information to the host, side communication part and that receives analysis result of the target substance from the host side communication part.

The third invention relates to the first or second invention and further has a classification information, acquisition part for acquiring classification information of the target substance. The information analysis part uses the classification information for the plasma light information based analysis of the target substance.

The fourth invention relates to the third invention. The information analysis part uses the classification information for selecting wavelength band of the plasma light that is used for the analysis of the target substance.

The fifth invention relates to the third or fourth invention. During the plasma light information based analysis of the target substance, the information analysis part narrows down the component of the target substance using the classification information.

The sixth invention relates to the third invention. A plurality of analysis programs that output results of the target substance corresponding to inputted plasma light information are prepared for types of the target substance. Based on the classification information, the information analysis part selects the analysis program that conforms to the type of the target substance.

The seventh invention relates to tire first or second invention, but further has a classification information acquisition part and a spectrum information generation part. The classification information acquisition part acquires the classification information of the target substance. The spectrum information generation part generates spectroscope information that is necessary for acquiring the wavelength band of the plasma light used for target substance analysis using the classification information. The spectroscope information is notified to the user of the analytical terminal.

The eighth invention relates to one of first to seventh invention. The analytical terminal acquires plasma light information by converting the plasma light of a predetermined wavelength band to an electric signal in the spectroscope that disperses the plasma light. The analytical terminal is configured so that the wavelength hand of the plasma light which is converted to an electric signal in the spectroscope is variable.

The ninth invention relates to one of first to eighth invention. The analytical terminal acquires location information where the plasma light information is acquired using GPS, and sends together the plasma light information and the location information to the host computer.

The tenth invention relates to ninth invention. The host computer makes a distribution chart of a particular substance from the plasma light information and the location information that are acquired from the plurality of the analytical terminal.

The eleventh invention relates to first or second invention. The analytical terminal acquires plasma light information of a manufactured product of a factory as a target substance. In the host computer, the information analysis part outputs inclusion information of a harmful substance as an analysis result of the manufactured product.

The twelfth invention relates to eleventh invention. A terminal other than the analytical terminal is registered as a notification destination for the inclusion information of harmful substance. The inclusion information of the harmful substance is notified to the other terminal when it is detected that the manufactured product includes harmful substance or when the manufactured product includes harmful substance of prescribed value or more.

The thirteenth invention relates to first or second invention. The analytical terminal acquires the plasma light information, of a substance inside a luggage as a target substance. In the host computer, the information analysis part outputs information indicating whether the luggage has a dangerous article or has a material of a dangerous article as an analysis result of the target substance.

Fourteenth invention relates to a provision system of analysis result comprising: an analytical terminal, a classification information, acquisition part, and a host computer. The analytical terminal is capable of using an analysis program that outputs the result of a target substance in response to an input of plasma light information. The plasma light information is acquired when the target substance is turned to a plasma state. A classification information acquisition part acquires classification information of the target substance and at least a portion of the classification information acquisition part is installed in the analytical terminal. The host computer is capable of communicating with the analytical terminal via a telecommunication line. The host computer selects an analysis program among a plurality of analysis program according to the classification information, and then sends information to the analytical terminal so that the analytical terminal can download the selected analysis program.

Fifteenth invention relates to an analytical terminal comprising: an analysis information acquisition means that turns target substance to plasma state and acquires plasma light information occurred from plasma area; and a communication means that sends the plasma light information through the telecommunication line.

Sixteenth invention relates to fifteenth invention. The analysis information acquisition means irradiates micro-waves to the target substance from a radiation antenna for maintaining plasma. A coating part for covering the target substance is formed on the surface of the analytical terminal, and the radiation antenna is installed at the coating part.

Seventeenth invention relates to fifteenth or sixteenth invention. The terminal further comprises a capturing device for taking a photograph. The plasma light is received by the photo detector of the capturing device and generates the plasma light information.

Eighteenth invention relates to one of fifteenth to seventeenth invention. The target substance is turned to plasma state by collecting laser light on the target substance surface using light collection optics. A focal point notification part is equipped for notifying focal point information of the light collection optics to the user of the analytical terminal when it is detected, that the focal point does not match with the target substance.

Nineteenth invention relates to one of fifteenth to eighteenth invention. This invention further comprises a camera shake notification part that notifies camera shake information to the user of the analytical terminal when the camera shake information of the user of the analytical terminal is detected while acquiring the plasma light information.

Twentieth invention relates to provision method of analysis result comprising following steps: (i) First step that analyzes a target substance using plasma light information in response to a receipt of the plasma light information from an analytical terminal via telecommunication line. The analytical terminal turns target substance to plasma state and acquires information of plasma light occurred from plasma area; (ii) Second step that sends an analysis result of the target substance acquired in the first step to the analytical terminal.

Advantage of the Present Invention

In the present invention, measures necessary for analyzing the target substance are separated into an analytical, terminal and a host computer. Plasma light information and analysis results of target substance are communicated using telecommunication line so that the analysis results of target substance are provided to a sender of the plasma light information. The analytical terminal can be made compact because some of the measures are not installed. Since the analytical terminal is portable, the plasma light information of a target substance can be acquired without transferring the target substance. Thus, the analysis result provision system can acquire an analysis result of a target substance without transferring the target substance.

BRIEF DESCRIPTION OF THE DRAWINGS

FIG. 1 illustrates an outlined structure of an analysis result provision system of a first embodiment.

FIG. 2 illustrates an outlined structure of an analytical terminal of the first embodiment.

FIG. 3 illustrates a time change of luminous intensity of plasma light of the first embodiment.

FIG. 4 illustrates a spectrum of plasma light of the first embodiment.

FIG. 5 illustrates an outlined structure of an analytical terminal of a first modification, of the first embodiment.

FIG. 6 illustrates an outlined structure of an analysis result provision system of a second modification of the first embodiment.

FIG. 7 illustrates an outlined structure of an analysis result provision system of a third modification of the first embodiment.

FIG. 8 illustrates an outlined structure of an analysis result provision system of a fourth modification of the first embodiment.

FIG. 9 illustrates an outlined structure of an analysis result provision system of a seventh modification of the first embodiment.

FIG. 10 illustrates an outlined structure of an analysis result provision system of a second embodiment.

DESCRIPTION OF THE PREFERRED EMBODIMENTS

The embodiments of the present Invention are detailed with reference to the accompanying drawings. The embodiments below are the preferred embodiments of the invention, but are not intended to limit the scope of present invention and application or usage thereof.

First Embodiment

The first embodiment relates to analysis result provision system 10 that analyze target substance 100 using plasma light when target substance 100 is turned to plasma state, and provides the analysis result of target substance 100 obtained from the analysis. As shown in FIG. 1, analysis result provision system 10 includes analytical terminal 11 and host computer 12. Analytical terminal 11 and host computer 12 are structured so that they can communicate each other by network 13.

Structure of the Analytical Terminal

Analytical terminal 11 is a terminal that consists of (1) a cellular phone having a telephone function, a network communication function, and a camera function; and (2) an analysis information acquisition function that acquires plasma light information necessary for analyzing target substance 100. As shown in FIG. 2, analytical terminal 11 has plasma generation unit 14 and spectrum unit 15 as the analysis information acquisition means that exercises the analysis information acquisition function. In analytical terminal 11, terminal side communication part 18 (communication means) functions as the network communication function.

Structure of the Plasma Generation Unit

Plasma generation unit 14 includes laser irradiation device 20, microwave radiation device 30, and controller 16. Plasma generation unit 14 turns target substance 100 to plasma state by laser irradiation device 20, and then maintains the plasma generated by laser irradiation device 20 using microwave radiation device 30 (these operations are collectively called "plasma generation operation").

Laser irradiation device 20 includes laser light source 21 and light collection optics 22, e.g. convex lens that collects laser light oscillated from laser light source 21. Laser light source 21 oscillates laser light for generating plasma when a laser oscillation signal is received from controller 16. Laser light source 21 is connected to light collection optics 22 that is held in lens holder 23 via an optical fiber (not illustrated). An incidence plane of light collection optics 22 faces an exit plane of the optical fiber. Exit plane of light collection optics 22 laces hemisphere hollow 24 formed on analytical terminal 11. Focal point of light collection optics 22 is located slightly outside of hollow 24.

In laser irradiation device 20, laser light oscillated from laser light source 21 refracts while passing light collection optics 22 and is then focused to the focal point of light collection optics 22. When target substance 100 is at the focal point of light collection optics 22, the energy density of the laser light at the focal point exceeds the breakdown threshold of target substance 100. Target substance 100 is thereby turned to plasma state.

Laser light source 21 is a small laser light source such as microchip laser and super luminescence diode. When the output of laser light source is small, multiple laser light sources 21 may be installed. In such case, light collection optics 22 may be installed for respective laser light source 21 to coincide the focal points of all light collection optics 22.

Microwave radiation device 30 includes microwave oscillator 33 and radiation antenna 32 for radiating microwave oscillated from microwave oscillator 31. Microwave oscillator 31 continuously outputs microwaves during the pulse width periods of a microwave drive signal when the microwave drive signal is received from controller 18. The microwave drive signal is a pulse signal of a constant voltage value. Microwave oscillator 31 is connected to radiation antenna 32 via microwave transmission line (not illustrated).

Radiation antenna 32 is installed so that the focal point of light collection optics 22 is included, in an intense electric field area. Radiation antenna 32 protrudes from hollow 24 of analytical terminal 11 so that the front lip of the antenna faces toward light collection optics 22. Front tip of radiation antenna 32 is located near the focal point of light collection optics 22.

Microwave oscillator 31 outputs 2.45 GHz microwaves. In microwave oscillator 31, a semiconductor oscillator generates microwaves. The semiconductor oscillator that oscillates other bandwidth of microwaves can be used also.

Structure of Spectrum Unit

As shown in FIG. 2, spectrum unit 16 includes optical probe 40 and spectroscope 41 for obtaining a luminescence spectrum of the light captured from optical probe 40. Spectrum unit 15 executes an information acquisition operation for acquiring plasma light information occurred from microwave plasma during a plasma maintenance period where plasma generation unit 14 maintains plasma using microwave energy.

Optical probe 40 is for capturing plasma light generated from microwave plasma that is in inside hollow 24. Optical probe 40 is structured such that an optical fiber is inserted inside a cylindrical casing. The exit side of the optical fiber of optical probe 40 is connected to an input terminal of spectroscopic 41.

Optical probe 40 is installed so that the plasma light occurred from the entire area of microwave plasma can be captured by optical fiber. Optical probe 40 is installed in hollow 24 so that the incident plane of the optical fiber faces the focal point of light collection optics 22. Instead of capturing the plasma light directly into the optical fiber, optical probe 40 may be configured such that the plasma light can be captured by optical fiber via lens.

Spectroscope 41 includes light distributor 41a, light receiver 41b, and conversion circuit 41c. Light distributor 41a is, for example, diffraction grating or prism and disperses plasma light captured by optical probe 40 to different directions according to wavelength. Light receiver 41b receives the plasma light dispersed by light distributor 41a and executes photoelectric conversion. Conversion circuit 41c converts an analog electric signal outputted from light receiver 41b to a digital signal. Light receiver 41b is a rectangular sensor (for example, CCD image sensor or multi-anode photomultiplier), where multiple light receiving elements (for example, charge-coupled device (CCD)) are arranged in one or more columns.

In spectroscope 41, the plasma light occurred from the optical fiber of optical probe 40 is dispersed to different directions in light distributor 41a according to the wavelength. Among the plasma light dispersed in light distributor 41a, the plasma light of predetermined wavelength band is receipt by light receiver 41b. The wavelength band of the light received by light receiver 41b will be the wavelength band of the analysis target. Light receiver 41b outputs an analog electric signal of the sensor which indicates the luminous intensity for every wavelength over the wavelength hand of the analysis target with a predetermined wavelength resolution while a CCD drive signal is received from controller 10. This analog signal is converted to digital signal in conversion circuit 41c. The digital information converted by conversion circuit 41c is plasma light information that includes luminescence spectrum of the plasma light. In light receiver 41b, period between the rising edge and the trailing edge of the CCD drive signal is an exposure period. Spectroscope 41 outputs plasma light information to memory 42.

Spectroscopic information, including wavelength band information of the analysis target and wavelength resolution information of light receiver 41b are pre-stored in memory 42. Plasma light information and the spectroscopic information are combined as analytical information, which will be used for analysis, and then is sent to host computer 12 from terminal side communication part 18.

Structure of Host Computer

Host computer 12 is a computer that is managed by a manager of analysis result provision system 10. As shown in FIG. 1, host computer 12 includes host side communication part 50, customer data creation part 51, information analysis part 52, and information accumulation part 53.

Host side communication part 50 sends and receives information between an external internet connection terminal such as analytical terminal 11 and general personal computer via network 13. When host side communication part 50 receives analytical information (plasma light information and spectroscopic information of the plasma light) from terminal side communication part 18 of analytical terminal 11, the analytical information is transferred to customer data creation part 51. Host side communication part 50 sends the analysis result back to analytical terminal 11, which sent the analytical information corresponding to this analysis result, when the analysis result of target substance 100 (described later) is received from customer data creation part 51.

Customer data creation part 51 creates customer data for customers using analysis result provision system 10, and updates the customer data upon usage of the customers. The customer data, corresponds to data for every user's of analytical terminal 11 registered in analysis result provision system 10. Each of the data consists of the user's individual information and the usage history of analysis result provision system 10. The individual information, consists of name, address, telephone number, E-mail address, or debit account number. The usage history of analysis result provision system 10 consists of, for example, analytical information, receipt date and time of the analytical information, and analysis result of the target substance obtained from the analytical information. The customer data created by customer data creation, part 51 is accumulated in information accumulation part 53.

The user of analytical terminal 11 needs to be registered to analysis result provision system 10 via analytical terminal 11, when the user uses analysis result provision system 10 for the first time. The user should access to website run by manager of analysis result provision system 10 and should input individual information (address, telephone number, E-mail address, and or debit account number). The individual information that is inputted to the website will be sent to host side communication part 50 via network 13. Host side communication part 50 sends a confirmation mail to the E-mail address of the individual information and sends the individual information to customer data creation part 51 when individual information is received. Customer data creation part 51 creates new customer data using the sent individual information. This customer data is stored in information accumulation part 53. Registration of a user is thereby completed. Passwords or electronic certifications can be used for securing the information security.

Every time the user of analytical terminal 11 uses analysis result provision system 10, information is created and then customer data creation part 51 transfers the information to information accumulation part 53. The usage history of analysis result provision system 10 of the user is then updated.

Information analysis part 52 receives analytical information from host side communication part 50 via customer data creation part 51. Information analysis part 52 then identifies the component of target substance 100 from received analytical information using an installed analysis program. Further, information analysis part 52 detects the density of identified component based on luminous intensity of the peak wavelength using a calibration curve. Identified name and density of the component will be the analysis results of target substance 100. Information analysis part 52 accesses information accumulation part 53 for identifying the component of target substance 100 and uses the database of information accumulation part 53.

Peak wavelength value of plasma light which occurs when a various substances are turned to plasma state, are stored in data base of information accumulation part 53. For example, the data base has sets of information of substance name and peak wavelength, e.g. peak wavelength of plasma light from copper (324.8 nm, 327.4 nm), lead (368.3 nm, 364.0 nm, 374.0 nm, 405.8 nm), molybdenum (379.4 mm), calcium (422.7 mm), cobalt (345.2 mm) and chrome (357.6 mm). Information accumulation part 53 accumulates the customer data as described above.

Operation of Analysis Result Provision System

Operation of analysis result provision system 10 will be described.

Once the user of analytical terminal 11 determines target substance 100 to be analyzed, the user approaches analytical terminal 11 to target substance 100 so that the part of or entirety of target substance 100 is covered by hollow 24 and presses the analysis button of input part 17. Then, in analytical terminal 11, controller 16 outputs a laser oscillation signal and a microwave drive signal, and a CCD drive signal.

Plasma generation unit 14 executes a plasma generation operation when the laser oscillation signal and the microwave drive signal are received. Spectrum unit 15 executes information acquisition operation when the CCD drive signal is received. The information acquisition operation is executed so as to synchronize with the plasma generation operation.

The microwave drive signal is a pulse signal which is outputted following the laser oscillation signal output. Pulse width of the microwave drive signal is set so that the microwave radiation period is tens milliseconds, for example. The CCD drive signal is a pulse signal which rises following the rising edge of the microwave drive signal, and falls before the falling edge of the microwave drive signal. Light receiving part 41b of spectroscopic 41 is activated during the microwave radiation period by CCD drive signal.

In the plasma, generation operation, laser irradiation device 20 oscillates a single pulse of laser light, and this laser light is collected to a focal point of light collection optics 22. Laser light energy is applied momentarily on the surface of target substance 100. As a result, the energy density of the laser light at the focal point of light collection optics 22 exceeds the breakdown threshold of target substance 100, and initial plasma is occurred from target substance 100.

Following an oscillation of the laser light, microwave radiation device 30 outputs microwaves from radiation antenna 32 in continuous wave (CW) before the initial plasma that is originated by the laser light disappears. In hollow 24, an intense electric field area, i.e. area where electric field strength is relatively strong in hollow 24, is formed near radiation antenna 32. As a result, initial plasma expands by absorbing microwave energy. Relatively large microwave plasma is thereby generated. The microwave plasma is formed so as to contact the surface part of target substance 100. The microwave plasma includes target substance 100 of plasma state. The microwave plasma is maintained during the microwave radiation period.

Microwave radiation device 30 can repetitively output the microwave pulse of predetermined duty from radiation antenna 32. In this case, the idle period of the microwave pulse is set such that new microwave pulses are outputted before the disappearance of the microwave plasma. Microwave plasma of relatively low energy can be thus maintained for adequate setting of the idle period.

FIG. 3 shows a time variation of plasma light occurred from plasma in a period between the initial plasma generation and the microwave plasma disappearance. First the luminous intensity peak of the initial plasma is seen momentary, and the luminous intensity then decreases to a minimum value near zero. After this minimum value, a luminous intensity increment period can be seen where the luminous intensity of microwave plasma increases. Following this microwave increment period, a luminous intensity constant period can be seen, and the luminous intensity of the microwave plasma is substantially constant (in other words, fluctuation of the luminous intensity is less than or equal to a predetermined value). Light receiving part 41b of spectroscopic 41 is activated during the luminous intensity constant period out of the microwave radiation period.

In the information acquisition operation, plasma light that occurred from the microwave plasma inside hollow 24 is captured by spectroscope 41 via optical probe 40. Spectroscope 41 creates plasma light information such as luminescence spectrum of the plasma light in the range of wavelength band out of the captured plasma light of the analysis target received by light receiving part 41b. Spectroscope 41 outputs the plasma light information to memory 42.

When these operations finishes, the monitor of analytical terminal 11 displays a notification message "Information acquisition of plasma light finishes" and a query message "Do you want to send the acquired plasma light information to manager of analysis result provision system 10 for analysis?". The monitor also displays charge (fee) which will be charged to the user for each analysis.

When the user presses a transmission button of input part 17 in response to these displays, controller 10 outputs a transmission instruction to terminal side communication part 18 so that the analytical information stored in memory 42 (consists of plasma, light information and spectroscopic information) is sent to host computer 12. Terminal side communication part 18 sends the analytical information to host computer 12 via network 18 when the transmission instruction is received.

In host computer 12, when host side communication part 50 receives analytical information, the analytical information, the sender's information of the analytical information (E-mail address) and the receipt date and the time information of the analytical information will be sent to customer data creation part 51. Customer data creation part 51 sends analytical information to information analysis part 52 when it is determined that the sender's customer data is existing based on the sender's information of the analytical information.

When the analytical information is received, information analysis part 52 initiates the analysis program. Information analysis part 52 detects the peak wavelength value in the wavelength band of the analysis target out of the received analytical information using the analysis program.

For example, information analysis part 52 creates spectrum information that indicates the luminous intensity change in the wavelength band of the analysis target. For example, a spectrum chart such as in FIG. 4 is created as the spectrum information. Information analysis part 52 detects peak wavelength where the peak of the luminous intensity appears in the spectrum information. Usually, multiple peak wavelengths are detected (sometimes, only one peak is detected). Information analysis part 52 uses database of information accumulation part 53 to identify the name of substance (atom or molecule) corresponding to detected peak wavelength and detects density of the identified substance. Information analysis part 52 sends the name of the identified substance and the density of the substance to customer data creation part 51 as the analysis result of target substance 100.

Customer data creation part 51 sends the analysis result of target substance 100 to information accumulation part 53 together with the analytical information and the receipt date and time of the analytical information so that the usage history in the users customer data can be updated. Customer data creation part 51 also sends the analysis result of target substance 100 to host side communication part 50.

Upon receipt of an analysis result of target substance 100, host side communication part 50 sends the analysis result of target substance 100 to the sender's analytical terminal 11 (E-mail address). In analytical terminal 11, terminal side communication part 18 receives the analysis result of target substance 100. In analytical terminal 11, the analysis result of target substance 100 is displayed on the monitor. The user of analytical terminal 11 can know the component of target substance 100 by seeing the monitor.

As discussed above, in analysis result provision system 10, when host computer 12 acquires plasma light information, target substance 100 is analyzed using the plasma light information. Then the analysis result of target substance 100 is sent to the sender of the plasma light information. The user of analytical terminal 11 presses the transmission button if the user accepts the fee to be charged according to the request of the analysis. Analysis result provision system 10 is a system that sends the analysis result of target substance 100 to the user, on condition that the user of analytical terminal 11 pays to the provider of the analysis result.

Advantage of the First Embodiment

In the first embodiment, measures that are necessary for analyzing target substance 100 are separated into analytical terminal 11 and host computer 12. The plasma light information and the analysis result of target substance 100 are communicated each other using network 13. The analysis result of target substance 100 is thereby provided to a sender of the plasma light information. Analytical terminal 11 can be made small because some of the measures are not installed. If analytical terminal 11 is portable, user can acquire plasma information without moving target substance 100. Thus, analysis result provision system 10 that can acquire the analysis result of target substance 100 without transmitting target substance 100 is realized.

Modification 1 of the First Embodiment

In this modification, analytical terminal 11 acquires plasma light information using a light detecting element of capturing device 60 that exercises camera function. As shown in FIG. 5, capturing device 60 includes a CCD image sensor 62 that receives light captured from camera lens 61 while a shutter is open, and an image processing part 63 that creates image information based on output information from CCD image sensor 62.

Analytical terminal 11 is a terminal that has analysis kit 36 installed on the top part of cellular phone body 35. Analysis kit 36 is installed removable to cellular phone body 35. Concave portion is formed in analysis kit 36 so that the top part of cellular phone body 35 can fit in. Connection terminals 37 and 38 for sending instruction to cellular phone body 35 from controller 10 are formed respectively on the top part of cellular phone body 85 and bottom surface of concave portion of analysis kit 36.

Analysis kit 36 has plasma generation unit 14, optical probe 40, and diffraction grating 43 similarly to the first embodiment. Optical probe 40, diffraction grating 43 (optical diffusion part), and CCD image sensor 62 (light receiving part) consists spectrum unit 15. Diffraction grating 43 diffuses the light received from optical probe 40. A predetermined wavelength band light out of the diffused light is received by CCD image sensor 62.

In this modification, when analysis button of input part 17 is pressed, plasma generation operation and information acquisition operation are executed. The description of the plasma, generation operation is omitted here because it is similar to the first embodiment.

In the information acquisition operation, the plasma light occurred from microwave plasma, enters diffraction grating 43 through optical probe 40. In diffraction grating 43, the incident plasma light is dispersed according to the wavelength.

During the microwave radiation period, a capture instruction signal and a skip instruction signal are input to capturing device 60 via connection terminals 37 and 38. When the capture instruction signal is received, capturing device 60 temporarily opens the shutter and applies driving voltage to CCD image sensor 62. While the shutter is open, the plasma light occurred from diffraction grating 43 reaches CCD image sensor 62 via camera lens 61.

CCD image sensor 62 creates plasma light information of wavelength band light received from the analysis target. When the skip instruction signal is received, capturing device 60 sends plasma light information directly to memory 42 skipping image processing part 63. Spectroscopic information, which is a combination of wavelength band information of analysis target and wavelength resolution information of CCD image sensor 62, is stored in memory 42.

Then, when the transmission button of input part 17 is pressed, controller 16 outputs a transmission instruction so that terminal side communication part 18 can send the analytical information, i.e. combined information of plasma light information and spectroscopic information that are stored in memory 42. Upon receiving the transmission instruction, the analytical information is sent to host computer 12. Since the operation of host computer 12 is similar to the first embodiment, detailed explanation will be omitted.

Analysis kit 36 can have light receiving part 41b so that the plasma light can be photoelectric converted, instead of using capturing device 60 of cellular phone body 35 for the conversion. In this case, analysis kit 36 includes plasma generation unit 14 and spectrum unit 15 of the first embodiment, and spectrum unit 15 of spectroscope 41 generates plasma light information. Plasma light information is stored in memory 42 of analysis kit 36 or of cellular phone body 35. When the transmission instruction is sent from controller 16, plasma light information is sent from terminal side communication part 18 of cellular phone body 35 to host side communication part 50.

Modification 2 of the First Embodiment

In this modification, an analysis program is selected among multiple analysis program based on the classification information of target substance 100. Here, the analysis program outputs component of target substance 100 and density of the component according to the inputted plasma light information. The classification information of target substance 100 is, for example, state information (solid, liquid or gas), material information (metal, wood, or soil), and metal information (aluminum, copper, or iron).

As shown in FIG. 6, analytical terminal 11 has capturing device 60. Capturing device acquires image information of target substance 100 by photographing target substance 100. This image information is input to information analysis part 52 together with the analytical information via network 13. If information analysis part 52 can recognize the correspondence between the image information and the analytical information, the image information and the analytical information can be input separately to information analysis part 52.

Information analysis part 52 executes a first analysis operation that detects the color of target substance 100, and existence, geometry and size of ruggedness based on an analysis of the image information. Then information analysis part 52 executes a second analysis operation that detects the material, e.g. wood, or metal, of target substance 100 as the classification information by analyzing the first analysis operation result using pattern recognition. In addition to capturing device 60, the first and second analysis operation portions of information analysis part 52 will be also included in classification information acquisition part 110.

Here, host computer 12 stores multiple analysis programs for various materials of target substance 100. Information analysis part 52 selects an analysis program that fits to the material detected in the second analysis operation among multiple programs. The component of target substance 100 is identified using the selected analysis program and density of the identified component is then detected.

The wavelength band information, for detecting the peak for various materials is set in each analysis program. Thus, peak detection does not have to be executed for every plasma light wavelength hand of the plasma light information, and can reduce the wavelength band for peak detection to a necessary range. The amount of the information processing required for the peak detection can thereby decrease.

In each analysis program, peak wavelengths for various substances are stored. Depending on the peak wavelength value, multiple substances having the same or neighboring peak wavelength might exist. In such case, the identification of the substance based on peak wavelength would be difficult if the material is unknown. On the contrary, substance that corresponds to the peak wavelength can be narrowed down because the different analysis program is used for different material in this modification. Therefore, the component can be identified accurately even when multiple substances having the same or neighboring peak wavelength exists.

Classification, information acquisition part 110 can use the name of the material of target substance 100 inputted by the user of analytical terminal 11 to input part 17 as the classification information, instead of using the image information. When the user of analytical terminal 11 inputs the material information of target substance 100 to input part 17 by characters, the inputted information is digitalized as classification information. The classification information is sent from terminal side communication part 18 to host side communication part 50, and is used for selecting the analysis program.

Instead of using different analysis program based on classification information, information analysis part 52 may select the peak detection wavelength hand (plasma light wavelength hand for identifying the component of target substance 100) using the classification information, information analysis part 52 may narrow down, the substance for the peak wavelength using classification information to identify the component of target substance 100 in the plasma light information based analysis of target substance 100.

Modification 3 of the First Embodiment

In this modification, the analysis program is provided from, the manager of host computer 12 to the user of analytical terminal 11. As shown in FIG. 7, the user of analytical terminal 11 can download an analysis program from website 115 that is administrated by a manager of host computer 12. In this case, information analysis part 52 that identifies the component of target substance 100 from the plasma light information using the analysis program is provided in analytical terminal 11. In this modification, the analysis result of target substance 100 can be acquired, using analytical terminal 11 only.

Similarly to the modification 2, the analysis program, can be selected awarding to the classification information of target substance 100. The selection of analysis program is done by host computer 12. Host computer 12 sends download information, i.e. hyperlink information of URL for downloading the selected analysis program to analytical terminal 11. Monitor of analytical terminal 11 displays a notification that fee will be charged, for the download, when the user of analytical terminal 11 selects a hyperlink of the URL, together with a button for downloading the selected analysis program. When the user of analytical terminal 11 selects a specific download button, the selected analysis program is downloaded to analytical terminal 11. This analysis program allows the analysis of target substance 100 in analytical terminal 11.

Modification 4 of the First Embodiment

As shown in FIG. 8, analysis result provision system 10 of this modification has spectroscopic information generation part 111 that generates spectroscopic information based on the classification information. The spectroscopic information relates to information of spectroscope 41 necessary for acquiring the wavelength hand of the plasma light that will be used for analyzing target substance 100, i.e. for identification of the component. Spectroscopic information generation part 111 is installed in host computer 12 in the example of FIG. 8, but spectroscopic information generation part 111 may be installed in analytical terminal 11.

Spectroscopic information is wavelength hand information of the plasma light which will, be received by light receiving part 41b of spectroscopic 41. The spectroscopic information generation part generates spectroscopic information such as "wavelength band for analyzing target substance 100 is 300 to 350 nm", when target substance is copper. This spectroscopic information is displayed on monitor 112 of analytical terminal 11.

Spectroscope 41 is removable from spectroscopic terminal 11. Spectroscope 41 can be changed depending on the wavelength band that light receiving part 41b of spectroscopic 41 can receive. This means that various spectroscope 41 that receives different wavelength band light can be used. The user of spectroscopic terminal 11 can see spectroscopic information displayed in the monitor and can attach spectroscope 41 to analytical terminal 11, where spectroscope 41 has light receiving part 41b receiving the light of 300 to 350 nm. Host computer 12 may send the hyperlink information, of the URL to analytical terminal 11 to notify where the spectroscope that matches the generation information can be purchased.

The spectroscopic information may be a model number of the spectroscopy. The parts of spectroscopic 41 such as prism, can be removable, and this part information (model number) (ran also be the spectroscopic information.

Modification 5 of the First Embodiment

In this modification, analytical terminal 11 is configured such that the wavelength band of plasma light, which will be converted to electrical signal in spectroscope 41, can be changed. To change the wavelength band, that light receiving part 41b receives, analytical terminal 11 has a movement mechanism that moves light receiving part 41b. The movement mechanism slides light receiving part 41b by the power outputted by the motor.

The movement mechanism controlled based on spectroscopic information for example. When the spectroscopic information, "wavelength band for analyzing target substance 100 is 300 to 350 nm" is created, the movement mechanism moves light receiving part 41b so that light receiving part 41b can receive the light of 300 to 350 nm out of the plasma light based on the spectroscopic information.

Modification 6 of the First Embodiment

In this modification, analytical terminal 11 uses GPS (Global Positioning System) for acquiring the location information that shows the location where the plasma light was acquired as well as acquiring the plasma light information. In this modification, the analysis result is acquired according to the location where the plasma light information was acquired.

In this case, analytical terminal 11 or host computer 12 may create distribution chart for certain substance, and then display the chart on the monitor of analytical terminal 11. For example, when a user of analytical terminal 11 acquires plasma light information at many locations in a mine, the distribution chart of the specific mineral can be created based on the analysis result and the location information of the multiple analysis points. In this modification, distribution chart of the specific substance is created based on the analysis result acquired from plasma light information in the multiple points and the location information that corresponds to each analysis results.

Modification 7 of the First Embodiment

Similarly to the modification 6, in this modification, analytical terminal 11 acquires location information that indicate the location where the plasma light was acquired using GPS as well as the plasma light information. As shown in FIG. 9, host computer 12 receives plasma light information and location information from multiple analytical terminals 11. Host computer 12 then creates a distribution chart of a specific substance, e.g. wide area distribution chart for one or more prefectures, based on the analysis result obtained, from the received plasma, light information and the location information corresponding to each analysis results. The distribution chart is created by distribution chart creation part 116.

Distribution chart, such as a density distribution chart of specific radioactive substance (cesium) or a density distribution chart of specific component (NOx) are created. Manager of analysis result provision system 10 provides the created distribution chart at their website on condition of payment. The distribution chart can be obtained from not only analytical terminal 11 but also from internet terminal 120 owned by public user.

The manager of analysis result provision system 10 may install analytical terminal 11 in multiple points for acquiring plasma light information at many locations in the wide area. Analytical terminal 11 can be installed in a moving vehicle such as automobile so that die user can drives the vehicle while acquiring the plasma light information and the location information. When many users who registered analytical terminal 11 to the analysis result provision system 10, the distribution chart can be created from plasma light information and location information that are collected from each users.

Second Embodiment

The second embodiment relates to quality inspection system 130 that uses analysis result provision system 10. As shown in FIG. 10, quality inspection system 130 inspects whether or not a harmful substance is included in target substance 100. Here, target substance 100 is manufactured product 100 such as food products that flow on production line 131 of factory 125.

Analytical terminal 11 is located, so that manufactured product 100 flowing on production line 131 of factory 125 can be turned to plasma state, and can acquire plasma light information of manufactured product 100. According to this quality inspection system 130, when a socially recognized harmful substance such as mercury (Hg) is detected from the analysis result of target substance 100, host computer 12 sends information indicating that a harmful substance is found as an inclusion information of the harmful substance to internet terminal 135 that is located in building 134, where analytical terminal 11 is not installed, as well as to analytical, terminal 11. The inclusion information is sent to internet terminal 135 of the management personnel of the company that owns factory 120. This internet terminal 135 is registered in analysis result, prevision system 10 as a terminal for notifying the detection of harmful substance.

According to the second embodiment, the management personnel can readily understand the existence of the harmful substance.

Information analysis part 52 may be installed in analytical terminal 11. In analytical terminal 11, component of manufactured product 100 is identified from plasma light information. In this case, when a socially recognized harmful substance such as mercury is identified according to the analysis result of target substance 100, the inclusion information of the harmful substance is sent to internet terminal 135 of management personnel from analytical terminal 11.

Third Embodiment

The third embodiment relates to a security system that uses analysis result provision system 10. Target substance 100 of this security system is a dangerous article that is inside a luggage. When target substance 100 inside the luggage is found out to be a dangerous article, this system notifies the existence of dangerous articles.

In analytical terminal 31, a needle shaped portion, that has a large diameter is provided for penetrating a wrapping of the luggage. Analytical terminal 11 generates plasma inside the luggage by irradiating laser light through, the needle shaped portion and introduces the generated plasma light to optical probe 40. In this case, plasma can be generated by using laser light only. Microwaves can be also used together with the laser light for generating plasma.

In the security system, analytical, terminal 11 turns the substance 100 inside the luggage to plasma state and acquires the plasma light information of target substance 100. Analytical terminal 11 acquires the location information that indicates the location where the plasma light was obtained using GPS, as well as the plasma light information. Analytical terminal 11 sends the location information to host computer 12 paired with the plasma light information.

In host computer 12, information analysis part 52 identifies the component of target substance 100 based on the received plasma light information and determines Whether or not the identified component is dangerous article. When the dangerous article is detected, host side communication part 50 sends the name of the dangerous article and the location information to the user of the security system (in this case, it may be government or local government).

When multiple dangerous articles are detected by information analysis part 52 from multiple luggage that are delivered to the same location, the warning information may be notified, to the system's user for informing that dangerous articles might be generated.

Other Embodiments

Following embodiment can be contemplated.

In the abovementioned embodiment, the function of host computer 12 of analysis result provision system 10 can be provided on a cloud computing system.

The analytical information, which is a combination of the plasma light information and the spectroscopic information, is sent from analytical terminal 11 to host computer 12 in the above embodiment. However, when host computer 12 stores the spectroscopic information, only the plasma light information may be sent to host computer 12 from analytical terminal 11.

The user of analytical terminal 11 can communicate with host computer 12 using a desktop or notebook personal computer instead of using analytical terminal 11. When the user of analytical terminal 11 acquired, the analytical information in the outdoors, the user can send the plasma light information to host computer 12 after returning to the building (research facility) and then transfer the plasma light information to the personal computer. The analysis result from host computer 12 is sent to the personal computer. The user of analytical terminal 11 can thereby confirm the analysis result using a large screen's display. The user of analytical terminal 11, can register multiple E-mail addresses to analysis result provision system 10.

In the above embodiment, analytical terminal 11 may have a focal point information notification part that notifies the focal point information of light-collection-optics 22 to the user of the analytical terminal when the focal point of light collection optics 22 is not in target substance 100. Analytical terminal 11 determines whether target substance 100 exists at the local point of light collection optics 22 or at its neighborhood by using supersonic wave. When it is detected that it does not exist, the monitor, of analytical terminal 11 displays that "The focal point of the lens (light collection optics) does not corresponds to the target substance". The focal point information of light collection optics 22 can be "Please adjust the position of analytical terminal 11". Accordingly, when the focal point of light collection optics 22 is detected that it is not in target substance 100 based on distance information from analytical terminal 11 to target substance 300, the user of analytical terminal 11 will be notified. Thus, even when the user of analytical terminal 11 does not have enough experience of analysis, the user can easily use analytical terminal 11. The notification setting for the notification can be released by the user. User can release the notification setting when the notification is unnecessary, for example, during the gas analysis.

Analytical terminal 11 may have a camera shake notification part that sends camera shake information to the user of analytical terminal 11 when a camera shake of the user of analytical terminal 11 is detected during the acquisition of the plasma light information. The monitor may display the information indicating that the analysis result may be inaccurate due to the camera shake. The monitor may display that re-analysis is required due to the camera shake.

A laser adjustment part for adjusting the output of the laser fight can be provided in input part 17. The user of analytical terminal 11 can control the amount of the laser light output. When target substance 100 cannot be fumed to plasma by laser light, the laser light output can be increased. The microwave adjustment part for adjusting the output of the microwave can be provided in input part 17. The user of the analytical terminal 11 can thereby control (increase or decrease) the microwave output.

In the above embodiment, the means for generating the initial plasma may be a discharge device that generates a spark discharge.

INDUSTRIAL APPLICABILITY

As discussed above, the present invention is useful, for an analysis result provision system that provides an analysis result of target substance obtained by analysis of the plasma light, an analytical terminal, and for a method of providing analysis result.

EXPLANATION OF REFERENCE NUMERALS

10 Analysis result provision system
11 Analytical terminal
12 Host computer
13 Network
50 Host, side communication, part
51 Customer data creation part
52 Information analysis part

The invention claimed is:
1. A system of providing an analysis result, comprising:
an analytical terminal that turns a target substance to plasma state and acquires plasma light information occurred from plasma area;
a host computer including
i) host side communication part that acquires plasma light information via telecommunication line, and
ii) information analysis part that analyzes the target substance using the plasma light information acquired by the host side communication part; and
a classification information acquisition part that acquires classification information of the target substance from which the plasma light information is acquired,
wherein the host side communication part transmits the analysis result of the target substance to the sender of the plasma light information, where the analysis result is obtained through the analysis of the information analysis part using the plasma light information, and
wherein the information analysis part performs the analysis of the target substance based on both the plasma light information and the classification information such that wavelength band of the plasma light that is used in the analysis of the target substance is selected according to the classification information.
2. The system as claimed in claim 1, wherein
the analytical terminal includes a terminal side communication part that sends plasma light information to the host side communication part and receives analysis result of the target substance from the host side communication part.
3. The system as claimed in claim 1,
wherein the information analysis part narrows down the components of the target substance using the classification information in the plasma light information based analysis of the target substance.
4. The system as claimed in claim 1,
wherein a plurality of analysis programs that output results of the target substance corresponding to inputted plasma light information are prepared for several types of target substance and
the information analysis part selects the analysis program that conforms to the type of the target substance based on the classification information.
5. The system as claimed in claim 1, further comprising:
a classification information acquisition part that acquires the classification information of the target substance;
a spectrum information generation part that generates spectroscope information necessary for acquiring the wavelength band of the plasma light used for target substance analysis using the classification information,
wherein the required spectroscope information is notified to the user of the analytical terminal.
6. The system as claimed in claim 1, wherein
the analytical terminal acquires plasma light information by converting the plasma light of a predetermined wavelength band to an electric signal in the spectroscope that disperses the plasma light, and
the analytical terminal is configured so that the wavelength band of the plasma light which is converted to an electric signal in the spectroscope is variable.

7. The system as claimed in claim 1,
wherein the analytical terminal acquires location information where the plasma light information is acquired using GPS, and sends the plasma light information in relation with the location information to the host computer.

8. The system as claimed in claim 7,
wherein the host computer makes a distribution chart of a particular substance from the plasma light information and the location information that are acquired from the plurality of the analytical terminal.

9. The system as claimed in claim 1, wherein
the analytical terminal acquires plasma light information of a manufactured product of a factory as a target substance and
in the host computer, the information analysis part outputs information regarding to an inclusion of a harmful substance as an analysis result of the manufactured product.

10. The system as claimed in claim 9, wherein
a terminal other than the analytical terminal is registered as a notification destination for the inclusion information of harmful substance, and
the inclusion information of the harmful substance is notified to the other terminal when it is detected that the manufactured product includes harmful substance or when it is detected that the manufactured product includes harmful substance of prescribed value or more.

11. The system as claimed in claim 1, wherein
the analytical terminal acquires the plasma light information of a substance inside a luggage as a target substance, and
in the host computer, the information analysis part outputs information indicating whether the luggage has a dangerous article or has a material of a dangerous article therein as an analysis result of the target substance.

12. A provision system of analysis result comprising:
an analytical terminal that is capable of performing analysis of a target substance by using an analysis program that outputs the result of the target substance in response to an input of plasma light information, wherein the plasma light information is acquired when the target substance is turned to a plasma state;
a classification information acquisition part that acquires classification information of the target substance, wherein at least a portion of the classification information acquisition part is installed in the analytical terminal; and
a host computer storing therein a plurality of analysis programs that utilize a different wavelength band of the plasma light according to the classification information of the target sub stance,
wherein the host computer is capable of communicating with the analytical terminal via a telecommunication line, selecting the analysis program among the plurality of analysis programs according to the classification information, and sending information to the analytical terminal so that the analytical terminal can download the selected analysis program and utilize the selected analysis program in the analysis of the target substance.

13. An analytical terminal comprising:
an analysis information acquisition means that turns target substance to plasma state and acquires plasma light information occurred from plasma area;
a classification information acquisition means that acquires classification information of the target substance; and
a communication means that sends the classification information and the plasma light information through the telecommunication line to a host computer that analyzes the target substance based on the classification information and the plasma light information.

14. The terminal as claimed in claim 13, wherein
the analysis information acquisition means irradiates microwaves to the target substance from a radiation antenna for maintaining plasma,
a coating part for covering the target substance is formed on the surface of the analytical terminal, and the radiation antenna is installed at the coating part.

15. The terminal as claimed in claim 13, wherein
the terminal further comprises a capturing device for taking a photograph, and
the plasma light is received by the photo detector of the capturing device and generates the plasma light information.

16. The terminal as claimed in claim 13, wherein
the target substance is turned to plasma state by collecting laser light on the target substance surface by light collection optics, and
the terminal comprises a focal point notification part that notifies a focal point information of the light collection optics to the user of the terminal when it is detected that the focal point does not match with the target substance.

17. The terminal as claimed in claim 13, further comprising:
a camera shake notification part that notifies camera shake information to the user of the analytical terminal when camera shake information of the user of the analytical terminal is detected while acquiring the plasma light information.

18. A method of analysis result comprising steps of:
a first step that analyzes a target substance using plasma light information in response to a receipt of the plasma light information from an analytical terminal via telecommunication line, wherein the analytical terminal turns target substance to plasma state and acquires the information of plasma light occurred from plasma area; and
a second step that sends an analysis result of the target substance acquired in the first step to the analytical terminal,
wherein the method further comprises a step that acquires classification information of the target substance, and
wherein the analysis of the target substance is performed based on both the plasma light information and the classification information such that wavelength band of the plasma light that is used in the analysis of the target substance is selected based on the classification information.

* * * * *